(12) United States Patent
Blomberg et al.

(10) Patent No.: US 9,753,019 B2
(45) Date of Patent: Sep. 5, 2017

(54) MEASURING NITRIC OXIDE IN FLUID

(71) Applicant: LifeHealth, LLC, Hopkins, MN (US)

(72) Inventors: Scott Everett Blomberg, Hopkins, MN (US); Mark Louis Peterson, Chanhassen, MN (US); Amanda Marie Franey, Princeton, MN (US)

(73) Assignee: LifeHealth, LLC DE (US)

( * ) Notice: Subject to any disclaimer, the term of this patent is extended or adjusted under 35 U.S.C. 154(b) by 353 days.

(21) Appl. No.: 14/155,346

(22) Filed: Jan. 14, 2014

(65) Prior Publication Data

US 2014/0197044 A1    Jul. 17, 2014

Related U.S. Application Data

(63) Continuation-in-part of application No. 13/843,562, filed on Mar. 15, 2013.

(60) Provisional application No. 61/752,435, filed on Jan. 14, 2013.

(51) Int. Cl.
    *G01N 27/416* (2006.01)
    *G01N 33/00* (2006.01)

(52) U.S. Cl.
    CPC ..... *G01N 33/0011* (2013.01); *G01N 33/0037* (2013.01)

(58) Field of Classification Search
    CPC ...... G01N 27/28; G01N 27/416; A61B 5/412; A61B 5/14546
    See application file for complete search history.

(56) References Cited

U.S. PATENT DOCUMENTS

| | | | |
|---|---|---|---|
| 5,459,076 A * | 10/1995 | Stamler | G01N 21/631 436/106 |
| 2011/0008815 A1* | 1/2011 | Stamler | A61B 5/0059 435/29 |
| 2014/0127081 A1* | 5/2014 | Fine et al. | 422/119 |
| 2014/0197043 A1 | 7/2014 | Blomberg et al. | |

FOREIGN PATENT DOCUMENTS

| CN | 105247340 A | 1/2016 |
|---|---|---|
| WO | WO-2007041164 A2 | 4/2007 |
| WO | WO-2014110605 A1 | 7/2014 |

OTHER PUBLICATIONS

"U.S. Appl. No. 13/843,562, Non Final Office Action mailed Aug. 14, 2015", 8 pgs.

(Continued)

*Primary Examiner* — Gurpreet Kaur
(74) *Attorney, Agent, or Firm* — Schwegman Lundberg & Woessner, P.A.

(57) ABSTRACT

Apparatus and methods in accordance with one or more preferred embodiments of the present invention are used to measure nitric oxide in a fluid, and each includes a sample injection port; a measurement chamber; an electromagnetic radiation source; one or controls and user interfaces; and a cartridge. The cartridge includes a sample chamber; an electromagnetic radiation and heat chamber; and a gas permeable membrane. The cartridge preferably is single-use and disposable. Further apparatus and methods in accordance with other alternative embodiments, and additional inventive aspects and features, are disclosed related to measuring nitric oxide in a fluid.

19 Claims, 7 Drawing Sheets

(56) References Cited

OTHER PUBLICATIONS

"U.S. Appl. No. 13/843,562, Preliminary Amendment filed Jul. 8, 2013", 5 pgs.
"U.S. Appl. No. 13/843,562, Response filed Sep. 23, 2015 to Non Final Office Action mailed Aug. 14, 2015", 7 pgs.
"International Application Serial No. PCT/US2014/011557, International Preliminary Report on Patentability mailed Jul. 23, 2015", 8 pgs.
"International Application Serial No. PCT/US2014/011557, International Search Report mailed May 29, 2014", 4 pgs.
"International Application Serial No. PCT/US2014/011557, Written Opinion mailed May 29, 2014", 6 pgs.
"U.S. Appl. No. 13/843,562, Non Final Office Action mailed Dec. 24, 2015", 10 pgs.
"U.S. Appl. No. 13/843,562, Response filed Apr. 25, 2016 to Non Final Office Action mailed Dec. 24, 2015", 8 pgs.
"Chinese Application Serial No. 201480015156.5, Voluntary Amendment filed Apr. 26, 2016", 6 pgs.
"U.S. Appl. No. 13/843,562, Non Final Office Action mailed Aug. 15, 2016", 17 pgs.
"U.S. Appl. No. 13/843,562, Notice of Allowance mailed Dec. 21, 2016", 8 pgs.
"U.S. Appl. No. 13/843,562, Response filed Nov. 15, 2016 to Non Final Office Action mailed Aug. 15, 2016", 11 pgs.

* cited by examiner

MEASURING NITRIC OXIDE IN FLUID

CROSS-REFERENCE TO RELATED APPLICATION

For purposes of the United States, the present application is a U.S. continuation-in-part patent application of, and claims priority under 35 U.S.C. §120 to, U.S. nonprovisional patent application Ser. No. 13/843,562, filed Mar. 15, 2013; and the present application is a U.S. nonprovisional patent application of, and claims priority under 35 U.S.C. §119(e) to, U.S. provisional patent application 61/752,435, filed Jan. 14, 2013. Each of these priority patent applications, and any patent application publication thereof and any patent issuing therefrom, are incorporated herein by reference. Moreover, the disclosure of the '435 provisional from which priority is claimed is included in the Appendix to the specification attached hereto, which Appendix is incorporated by reference herein.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

As a preliminary matter, a method is known for measurement of NO concentration in a blood sample by (introducing the blood sample to a chamber; directing low-power electromagnetic radiation to liberate the NO molecule from various bound molecules; providing vaporization to liberate NO as a gas; and measuring liberated NO gas using an electrochemical method. A laser or light emitting diode (LED) provides the low-power electromagnetic radiation. Such a conventional method is disclosed in U.S. Patent Application Publication No. 2011/0008815, incorporated by reference herein.

SUMMARY OF THE INVENTION

The present invention generally relates to methods and apparatus for measuring nitric oxide in fluid, and the present invention includes many aspects and features, which are disclosed herein.

In a first aspect of the invention, a method for measuring a dissolved gas in a fluid comprises the steps of: liberating the dissolved gas from the fluid; capturing the liberated gas in a carrier gas; and measuring the dissolved gas concentration using an electrochemical sensor.

In a feature, the dissolved gas is nitric oxide.

In a feature, the method further includes the steps of freeing the gas from its molecular bonds using electromagnetic radiation; and outgassing the dissolved gas from the fluid. The electromagnetic radiation may be generated using one or more light emitting diodes (LEDs) in one or more preferred embodiments of the invention. The outgassing method preferably is by heat vaporization in one or more preferred embodiments of the invention.

In another feature of this aspect, the method for capturing the liberated gas is closed from ambient atmosphere.

In another aspect, an apparatus for measuring nitric oxide in a fluid comprises a disposable component for containing liquid or solid residue from a fluid sample; and a reusable instrument component comprising a pump, one or more valves, a nitric oxide sensor, one or more controls and one or more user interfaces. The disposable component preferably is a disposable cartridge.

In a feature, the disposable component is designed for a single use.

In a feature, the disposable component contains means for liberating nitric oxide gas from the fluid. The means for liberating nitric oxide gas from the fluid preferably includes an electromagnetic radiation source in one or more preferred embodiment of the invention. The electromagnetic radiation source preferably is a component of the instrument and not the disposable component, and the electromagnetic radiation source comprises one or more light emitting diodes in one or more preferred embodiments of the invention.

In a feature, the disposable component contains means for liberating nitric oxide gas from the fluid. The means for liberating nitric oxide gas from the fluid preferably includes means for outgassing the nitric oxide gas from the fluid.

In a feature, the one or more controls and one or more user interfaces include a microprocessor.

In a feature, the sensor for measuring nitric oxide gas is an electrochemical sensor.

In a feature, the apparatus includes a means for capturing the nitric oxide containing gas, which preferably is closed to ambient atmosphere.

In a feature, the disposable component includes a means for containing the liquid and solid components of the fluid sample, and may comprise a gas permeable membrane in one or more preferred embodiments of the invention.

In another aspect, an apparatus for measuring nitric oxide in a fluid, comprising: a gas pump; a valve; a measurement chamber; an electromagnetic radiation source; a heater; control and user interface; and a cartridge comprising a sample chamber, a sample degassing chamber, and a reaction chamber.

In another aspect, an apparatus for measuring nitric oxide in a fluid comprises a sample injection port; a pump and reservoir; a valve; a measurement chamber; an electromagnetic radiation source; control and user interface; and a cartridge comprising a sample chamber, a mix chamber, a sample degassing chamber, and a planar reaction chamber.

In a feature, the cartridge is disposable and is designed for a single use.

In yet another aspect, a method for measuring a dissolved gas in a fluid comprising the steps of: liberating the dissolved gas from the fluid; measuring the liberated gas in a carrier gas; and measuring the dissolved gas concentration using an electrochemical sensor. The method of liberating the dissolved gas from the fluid preferably includes cleaving the gas from its molecular bonds using electromagnetic radiation, heat, or both; and liberating the dissolved gas from the fluid. Electromagnetic radiation is used in one or more preferred embodiments, which preferably is generated using one or more light emitting diodes. Liberating the dissolved gas is alternatively or additionally accomplished by heat vaporization or fluid exasperation.

In another aspect, an apparatus for measuring nitric oxide in a fluid comprises a disposable component for containing liquid or solid residue from fluid sample; and an reusable instrument component comprising a pump, a nitric oxide sensor, and one or more controls and user interfaces.

In a feature, the disposable component is designed for a single use.

In a feature, the disposable component contains a means for liberating nitric oxide gas from the fluid.

In a feature, the one or more controls and user interfaces comprise a microprocessor.

In a feature, the sensor for measuring nitric oxide gas is an electrochemical sensor.

In a feature, the apparatus comprises a means for capturing the nitric oxide containing gas.

In another aspect, an apparatus for measuring nitric oxide in a fluid comprises: (a) a gas pump; (b) a measurement chamber; (c) an electromagnetic radiation source; (d) a heater; (e) one or more controls and user interfaces; and (f) a cartridge comprising a sample chamber, a reaction chamber, a gas permeable membrane, and a sample injection port.

Another aspect comprises an apparatus for measuring nitric oxide in a fluid as disclosed and described herein.

Another aspect comprises a method for measuring nitric oxide in a fluid as disclosed and described herein.

BRIEF DESCRIPTION OF THE DRAWINGS

One or more preferred embodiments of the present invention now will be described in detail with reference to the accompanying drawings, wherein the same elements are referred to with the same reference numerals, and wherein.

DETAILED DESCRIPTION

Figure 1:
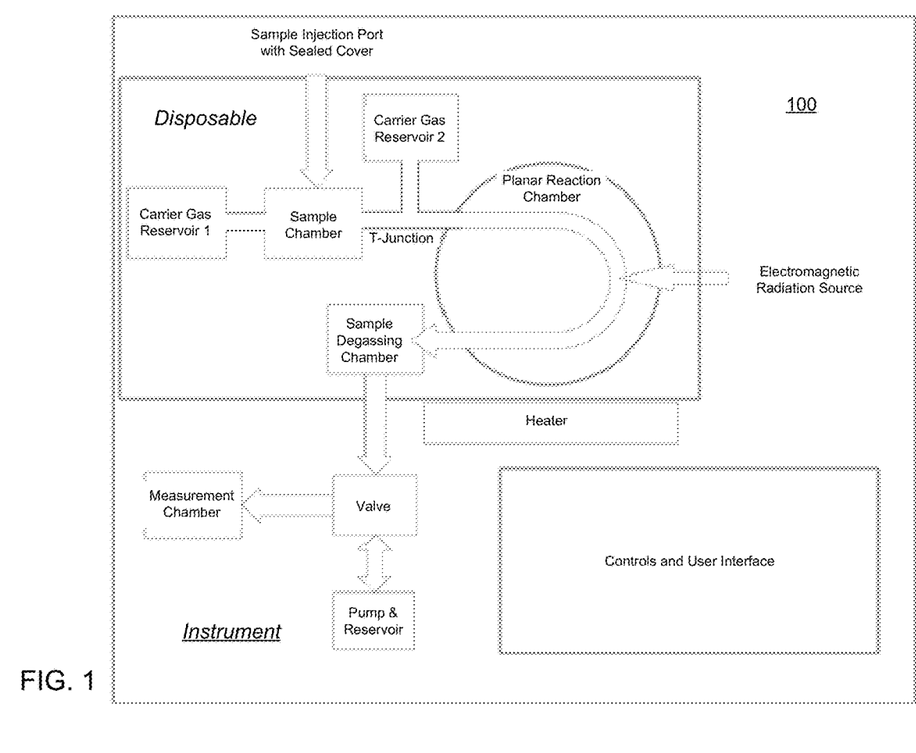
FIG. 1 illustrates a system block diagram in accordance with one or more embodiments of the present invention.

In accordance with one or more preferred embodiments of the present invention, which are now described in detail with reference to the system block diagram 100 of FIG. 1 in accordance with one or more embodiments of the present invention, a Sample Injection Port (simple luer or needle safe port) is provided for injecting blood or other fluid containing Nitric Oxide into a sample chamber for containing the fluid sample prior to analysis. The Sample Injection Port includes a sealed cover containing the sample in the disposable after injection. The sample chamber is an enclosure into which fluid is stored after being injected into the Sample Injection Port. Two carrier gas reservoirs are provided (Carrier Gas Reservoir 1 and Carrier Gas Reservoir 2). After the cover on the Sample Injection Port is closed and sealed, the Sample Chamber is only connected to Carrier Gas Reservoir 1 on one side and a T-Junction on the other side. The T-Junction is also connected to Carrier Gas Reservoir 2. Both carrier gas reservoirs are approximately the same volume (0.1 ml to 1 ml), contain room air carrier gas and are sealed from outside air. This arrangement allows for the fluid sample to mix with gas from Carrier Gas Chamber 2 simply by pulling the sample through the T-Junction with negative pressure. The size of the individual mixed fluid droplets can be adjusted by adjusting the relative volume of the two carrier gas chambers.

The sample mixture is directed into a planar reaction chamber with at least one surface highly transparent to electromagnetic radiation. While the sample mixture is within this chamber, it is exposed to the radiation and heated thus driving the desired chemical reaction which liberates nitric oxide from the blood.

The disposable cartridge includes a sample degassing chamber. This chamber removes the dissolved NO gas from the fluid sample and keeps all fluid and non-gaseous components of the fluid inside the cartridge. The chamber may comprise a heated surface which drives the outgassing of the fluid through heat vaporization. The chamber may also include a simple gravity mechanism whereby the fluid/gas mixture enters at the bottom and only gas is pumped out at the top leaving fluid and solids behind by the force of gravity. An alternative chamber design includes a gas-permeable hydrophobic membrane which allows for the gaseous components of the fluid/gas mixture to pass and prohibits the passage of fluid. Preferred embodiments include both heat vaporization and a membrane, which acts as a secondary containment mechanism for the fluid and solids left behind after degassing.

The design and construction of the disposable cartridge is such that it can be inexpensively manufactured using common materials such as polymers and manufacturing methods such as molding, thermoforming, extruding and stamping.

With greater regard to the instrument, it contains a programmable pump and valve for the control of gas into and out of the disposable cartridge and into the measurement chamber where the NO gas is measured. The instrument also contains the electromagnetic radiation source, such as a mercury high pressure bulb, metal halide bulb, lasers, LED's or laser diodes, emitting a radiation primarily in the 325-450 nm wavelength range and/or secondarily in the 290-325 nm wavelength range and/or in the 450-600 nm wavelength range. Preferred embodiments comprise LEDs, as LEDs are believed to be smaller, less expensive, draw less power, and generate less heat than the other radiation sources. In addition, the instrument includes microprocessor controller(s) for automated operation, a user interface, and data memory/communication capabilities.

The instrument also includes a sample measurement chamber for measuring nitric oxide gas and quantifying its concentration. In preferred embodiments, the sample measurement chamber is connected to an amperometric electrochemical nitric oxide gas sensor. The sample gas, which includes the nitric oxide and carrier gas, enters the sample measurement chamber and diffuses into the electrochemical sensor. The electrochemical sensor has been optimized for the concentrations in the range of 2 parts per billion (ppb) to 5 parts per million (ppm). The sample measurement chamber is 0.1 to 0.5 milliliter in volume. Alternative methods for measuring nitric oxide include chemiluminescence and spectroscopic fluorescence. For these alternatives, the sample measurement chamber would be designed as appropriate for those methods.

With the exception of the sample measurement chamber, the entire system preferably is sealed from the outside environment once the disposable cartridge is inserted into the instrument. It is believed that this is an important feature to controlling the amount of carrier gas within which the NO gas sample is measured. The fluid/gas sample is moved throughout the system by varying the relative pressure of the gas throughout the system using the pump and reservoir.

Figure 2:
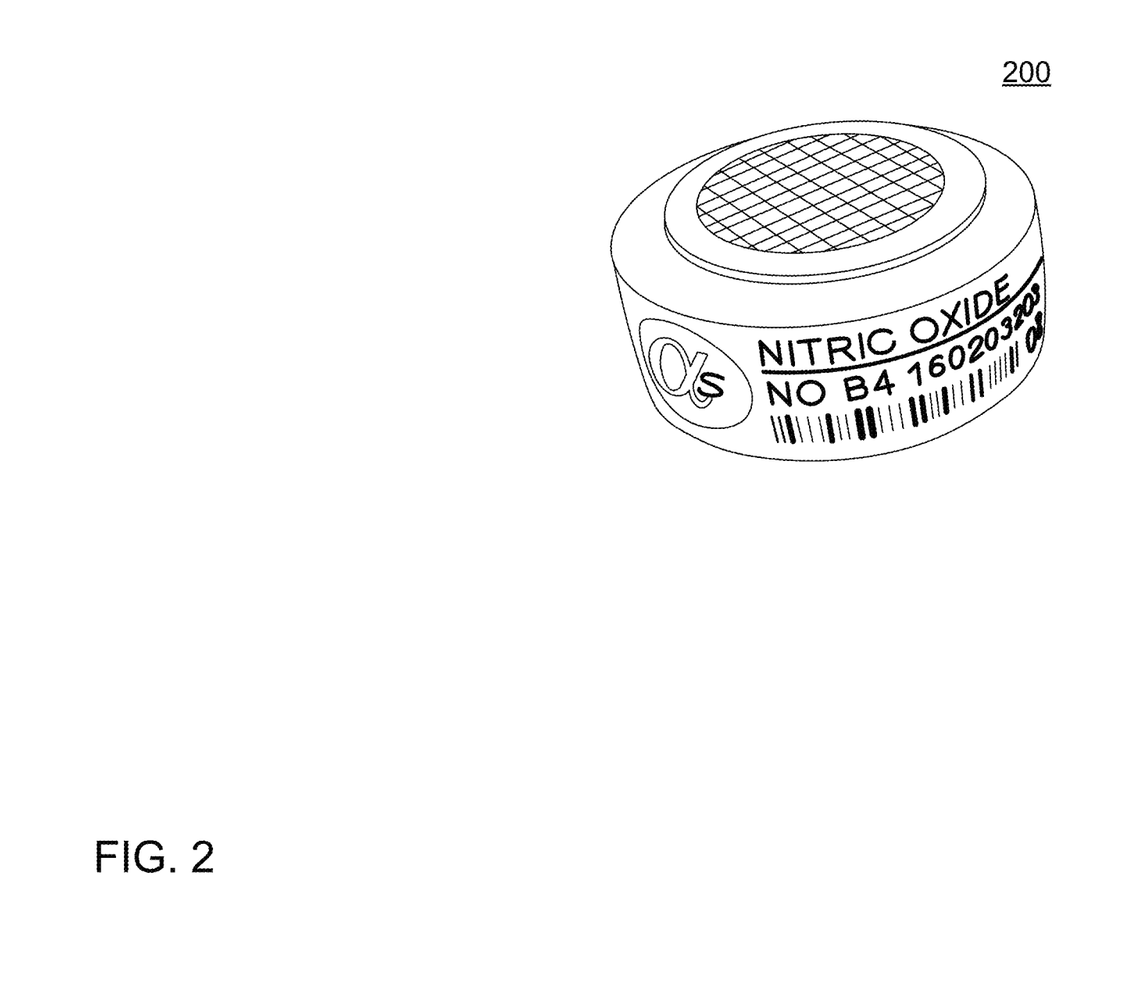
FIG. 2 illustrates a commercially available electrochemical nitric oxide sensor and is exemplary of a component of one or more embodiments of the present invention.
Figure 3:
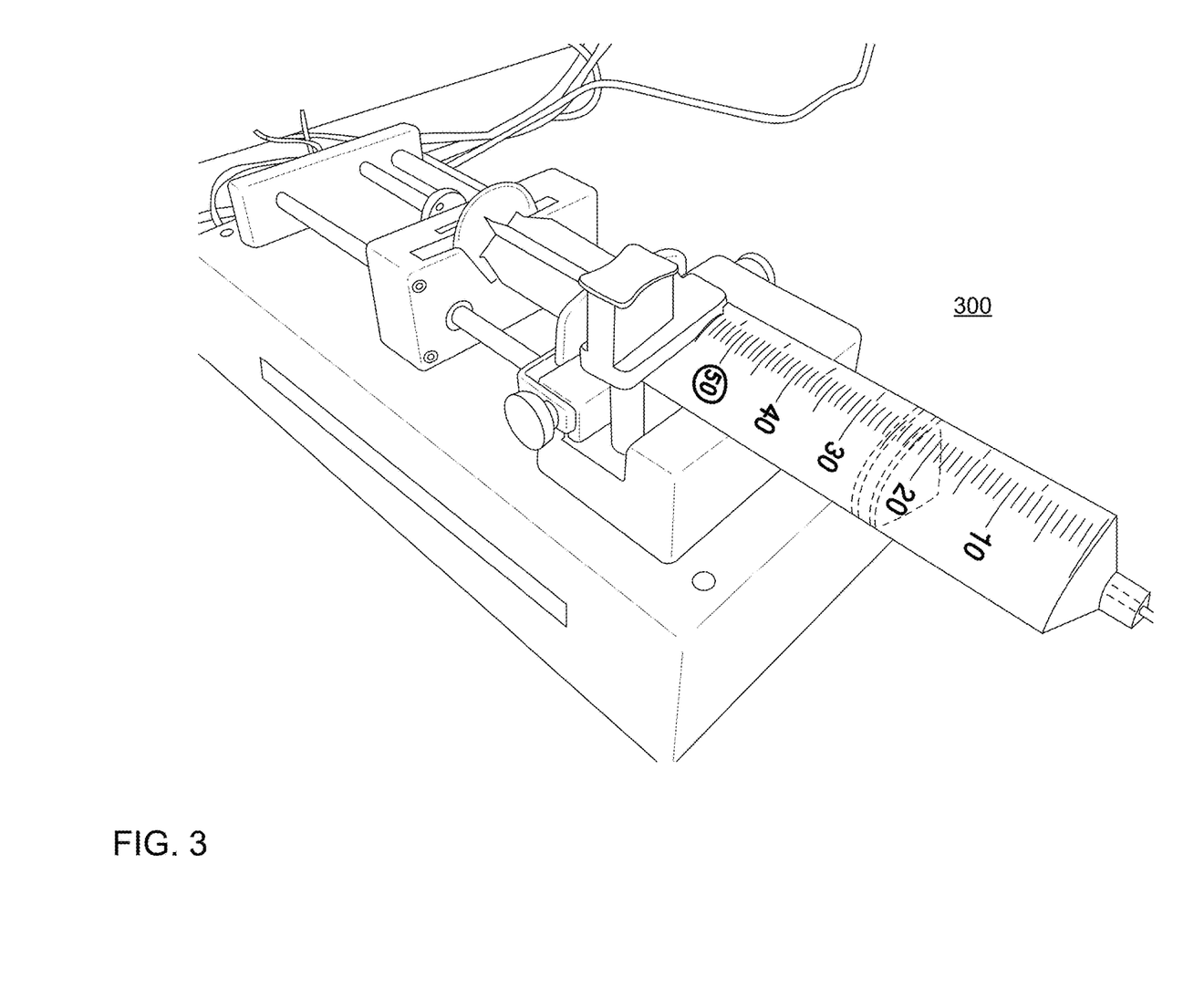
FIG. 3 illustrates a commercially available syringe pump and is exemplary of a component of one or more embodiments of the present invention.
Figure 4:
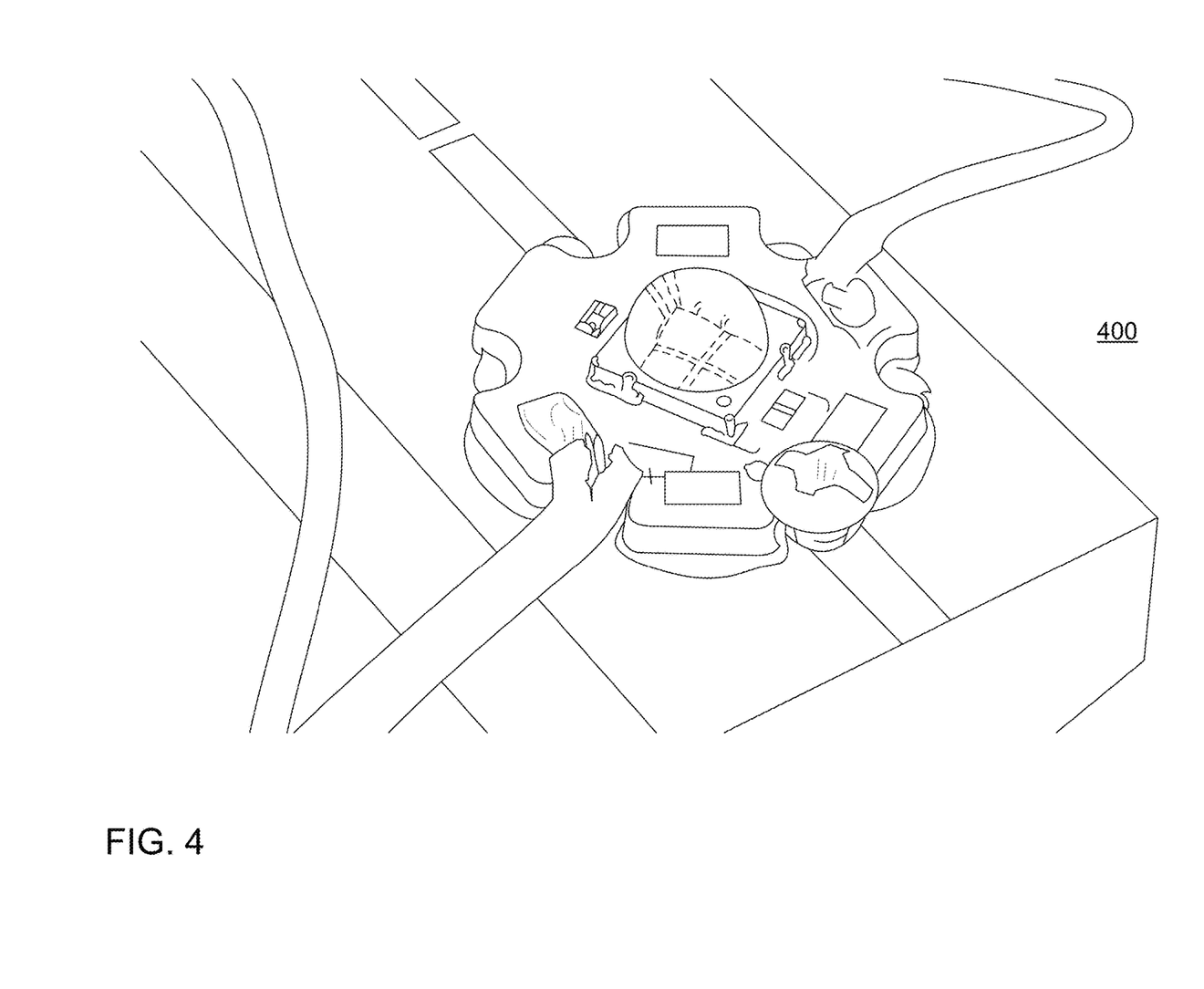
FIG. 4 illustrates a commercially available radiation source and is exemplary of a component of one or more embodiments of the present invention.
Figure 5:
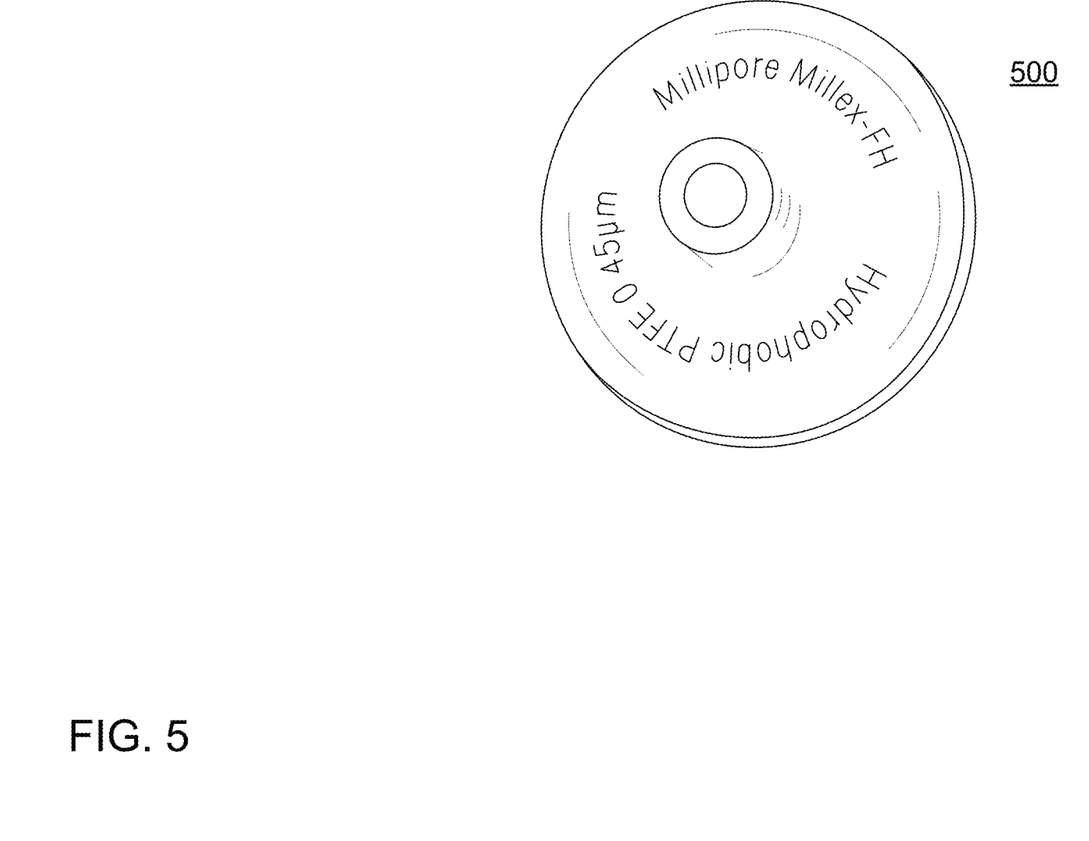
FIG. 5 illustrates a commercially available syringe filter and is exemplary of a component of one or more embodiments of the present invention.

FIG. 2 is an illustration of a commercially available electrochemical nitric oxide sensor 200 from Alphasense, Great Notley, Essex, United Kingdom; FIG. 3 is a commercially available syringe pump 300 from New Era Pump Systems, Inc. Farmingdale, N.Y., US; and FIG. 4 is an illustration of a commercially available radiation source 400 comprising a 365 nm UV light emitting diode (LED) available from LED Engin, Inc., San Jose, Calif., US; and FIG. 5 is a commercially available syringe filter 500 and is exemplary of a component of one or more embodiments of the present invention.

With respect to operation of preferred embodiment, the disposable cartridge is inserted into the instrument and the user is asked to inject the sample, typically 25 to 100 microliters into the sample injection port (thus directing the liquid sample into the Sample Chamber), close its sealed cover and select start. Operation after that is fully automated and includes the following steps:

The instrument's pump (syringe or positive displacement) pulls gas out of system thereby reducing the pressure in the Photolysis Chamber, typically to 100 to 500 millibars. The exhausted carrier gas is stored in a reservoir or alternatively exhausted to reduce total amount of system gas and lower relative system pressure.

The pump continues to pull gas out of the system which causes the sample fluid to move toward the Photolysis Chamber automatically mixing with gas from Carrier Gas Reservoir 2 at the T-Junction creating a liquid/gas mixture. After passing through the T-Junction the liquid/gas mixture enters the Planar Reaction Chamber.

In the Planar Reaction Chamber the sample is exposed to the Electromagnetic Radiation resulting in a chemical reaction. The resulting chemical reaction is nitric oxide (NO) liberated from its bonds to other molecules and becoming a dissolved gas in the fluid. Some NO is immediately degassed out of the fluid via diffusion.

The liquid/gas mixture is then pumped into the Degassing Chamber by the pump thus continuing to reduce pressure through the system.

While passing through the Degassing Chamber, NO is released from the fluid sample by one of the methods described. In the preferred method, the fluid is heated to vaporization outgassing the NO.

The Pump continues to withdraw the majority of the photolysis gas mix into the Pump and Reservoir Chamber.

The instrument's valve is closed sealing the pump and reservoir from the rest of the system. The Pump returns pressure of the gas mix to atmospheric pressure which is optimal for the electrochemical gas sensor.

The valve is opened to the sensor and the Pump directs the photolysis gas mix into the sensor chamber. The sensor measures sample NO in gas form as a fractional percentage of the entire gas sample including the carrier gas. The concentration of the gas is in the range of 2 parts per billion (ppb) to 5 parts per million (ppm). These concentrations correlate to the initial concentration of the bound nitric oxide in the fluid sample. These concentrations are in the range of 10 nanomolar (nM) to 10 micromolar (M). With respect to contemplated alternatives to the foregoing, the Photolysis Chamber may be one of several shapes provided that a sufficient amount of electromagnetic radiation is imparted on the sample during the measurement. These shapes could include a zigzagging maze, a multilevel spiral or a planar spiral as shown.

Additionally, the disposable cartridge could be used once or multiple times. In addition, the features of the Disposable Cartridge could be incorporated into a reusable system. This system would also then include a way of cleaning itself between individual measurements.

Other methods for measuring NO gas concentration in the measurement chamber also could be utilized, including a spectrophotometric method, a photo-colorimetric method, or a chemiluminescence method.

One or more aspects and features of the present invention include: a disposable cartridge that contains all of the non-gaseous fluid components; NO blood measurement using an electrochemical gas sensor; a disposable cartridge in which a sample is combined with a carrier gas, in which photolysis is performed on the sample, and in which any non-gaseous components from the sample are filtered-out; a cartridge construction that is compact thus allowing for easy insertion and removal for disposal; a completely closed NO extraction method which includes mixing of fluid with gas carrier, radiation to drive NO cleavage, outgassing of NO and separation from fluid/solids sample all within a closed system; and pre-pressurization of such a closed system.

It is believed that one or more advantages of one or more embodiments of the present invention include keeping all non-gaseous components of a fluid sample especially blood in the disposable cartridge reduces or eliminates the need to clean the Analysis Instrument thus making the device easier to maintain; electrochemical gas sensors are smaller, less expensive and easier to maintain than other sensing methods such as fluorescent spectroscopy and chemiluminescence. (in addition, by measuring NO in gas form, this method is less complex and thus more reliable than the previously disclosed method where electrochemical fluid NO sensors were used); a compact Disposable Cartridge design enables the entire test to be automated since all functions are performed together (this makes the device easier to use than previous devices and will require less maintenance); and having a closed system which greatly enhances the ability to measure extremely low concentrations (ppb) (pre-pressurization further enhances this).

Still yet additional apparatus and methods for detecting nitric oxide in a fluid are disclosed in the invention disclosures forms of the Appendix of the priority applications identified above, which is incorporated by reference herein and which forms part of the disclosure of embodiments of the present invention.

Figure 6:
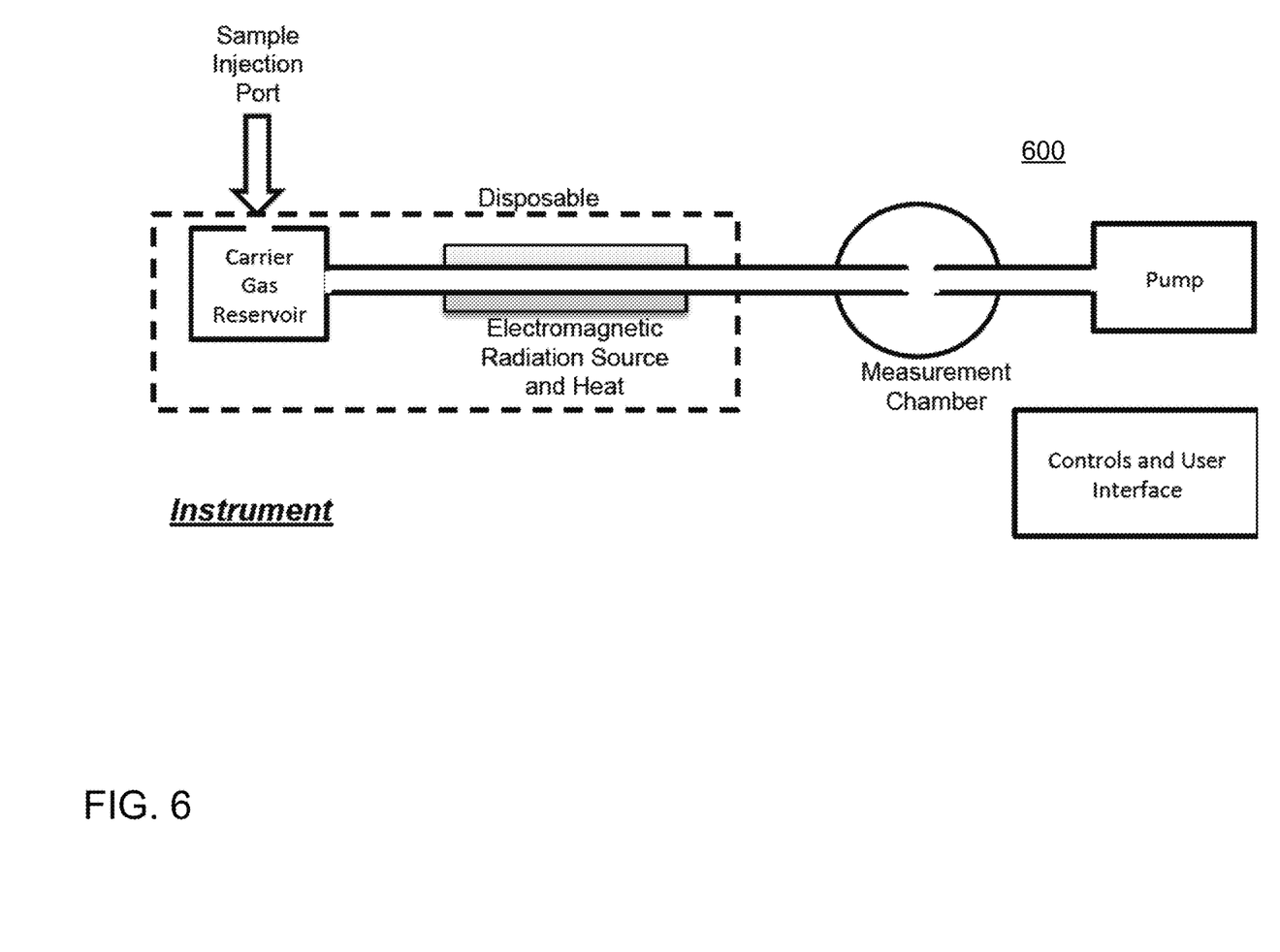
FIG. 6 illustrates another system block diagram in accordance with one or more embodiments of the present invention

In accordance with additional, preferred embodiments of the present invention, described in detail with reference to the system block diagram of FIG. 6, a Sample Injection Port is provided for blood or other NO containing fluid injection, it contains the fluid prior to analysis. The sample is injected in droplets, primarily four 10 µL (microliter) droplets (for 40 µL sample) or eight 5 µL droplets. The individual droplets create a room air carrier gas between each droplet.

The sample mixture is directed into a reaction chamber where it is exposed to electromagnetic radiation and heated. This causes the desired chemical reaction and nitric oxide is liberated from the blood. The heat assists in the exasperation of NO gas from the liquid sample through heat vaporization.

Upon release from the reaction chamber the sample enters a chamber including a gas-permeable hydrophobic membrane allowing the gaseous components of the fluid/gas mixture to pass and prohibits the passage of fluid.

The design and construction of the disposable cartridge is such that it can be inexpensively manufactured using common materials such as polymers and manufacturing methods such as molding, thermoforming, extruding and stamping.

With respect to the instrument (non-disposable component), it contains a programmable pump for the control of gas through the disposable cartridge and into the measurement chamber where the NO gas is measured. The instrument also contains the electromagnetic radiation source, such as a mercury high pressure bulb, metal halide bulb, LASERs, LED's or laser diodes; emitting radiation primarily in the 325-450 nm wavelength range and/or secondarily in the 290-325 nm wavelength range and/or in the 450-600 nm wavelength range. Preferred embodiments comprise LEDs, as LEDs are believed to be smaller, less expensive, draw less power, and generate less heat than the other radiation sources. In addition, the instrument includes microprocessor controller(s) for automated operation, a user interface, and data memory and communication capabilities.

The instrument also includes a sample measurement chamber for measuring nitric oxide gas and quantifying its concentration. In preferred embodiments, the sample measurement chamber is connected to an amperometric electrochemical nitric oxide gas sensor. The sample gas, which includes the nitric oxide and carrier gas, enters the sample measurement chamber and diffuses into the electrochemical sensor. The electrochemical sensor has been optimized for the concentrations in the range of 2 parts per billion (ppb) to 5 parts per million (ppm). Alternative methods for measuring nitric oxide include chemiluminescence and spectroscopic fluorescence. For these alternatives, the sample measurement chamber would be designed as appropriate for those methods.

An exemplary amperometric electrochemical nitric oxide sensor is commercially available from Alphasense, Great Notley, Essex, United Kingdom; an exemplary syringe pump is a commercially available from New Era Pump Systems, Inc., Farmingdale, N.Y., US; and an exemplary radiation source mounted on a custom circuit board and having nine 365 nm UV light emitting diodes (LEDs) is commercially available from LED Engin, Inc., San Jose, Calif., US.

With respect to operation of preferred embodiment, the sample is injected into the injection port of the disposable cartridge, typically 25 to 100 microliters (per the aforementioned droplet sizes), the disposable cartridge is then inserted into the instrument and the user selects start. Operation at that point is fully automated and includes the following steps:

The instrument's pump (syringe or positive displacement) pulls gas through the system, causing the fluid sample to move through the Reaction Chamber (electromagnetic radiation source and heat) and finally reaches the electrochemical nitric oxide sensor.

The resulting chemical reaction is nitric oxide liberated from other molecules. Some NO is immediately outgassed from the fluid via diffusion while more is outgassed with the heat vaporization. Alternatively, outgassing may be accomplished by fluid exasperation whereby the fluid is agitated to promote liberation of the dissolved gas.

The liquid/gas mixture is pulled through the gas-permeable hydrophobic membrane. Where the liquid/solids is contained in the membrane allowing the carrier gas and NO pass through to the sensor.

The sensor measures sample NO gas as a fractional percentage of the entire gas sample including the carrier gas. The concentration of the gas is in the range of 2 parts per billion (ppb) to 5 parts per million (ppm). These concentrations correlate to the initial bound concentration of nitric oxide in the fluid sample. In blood these concentrations are in the range of 10 nanomolar (nM) to 10 micromolar ($\mu$M).

Other methods for measuring NO gas concentration in the measurement chamber also could be utilized, including a spectrophotometric method, a photo-colorimetric method, or a chemiluminescence method.

One or more aspects and features of these additional, preferred embodiments include: NO blood gas measurement using an electrochemical gas sensor; a disposable cartridge in which a sample is combined with a carrier gas, in which photolysis is performed on the sample, and in which any non-gaseous components from the sample are filtered-out; and a cartridge construction that is compact, allowing for easy insertion and removal for disposal.

It is believed that one or more advantages of one or more such additional, preferred embodiments include: keeping all non-gaseous components of a fluid sample, especially blood, in the disposable cartridge reduces or eliminates the need to clean the instrument making the device easier to maintain; economical design, as electrochemical gas sensors are smaller, less expensive and easier to maintain than other sensing methods such as fluorescent spectroscopy and chemiluminescence (in addition, by measuring NO in gas form, this method is less complex and thus are believed perhaps to be more reliable than where electrochemical fluid NO sensors are used); and, as many functions are performed simultaneously, a compact cartridge design enables the test to be automated, thereby reducing user and maintenance requirements.

Figure 7:
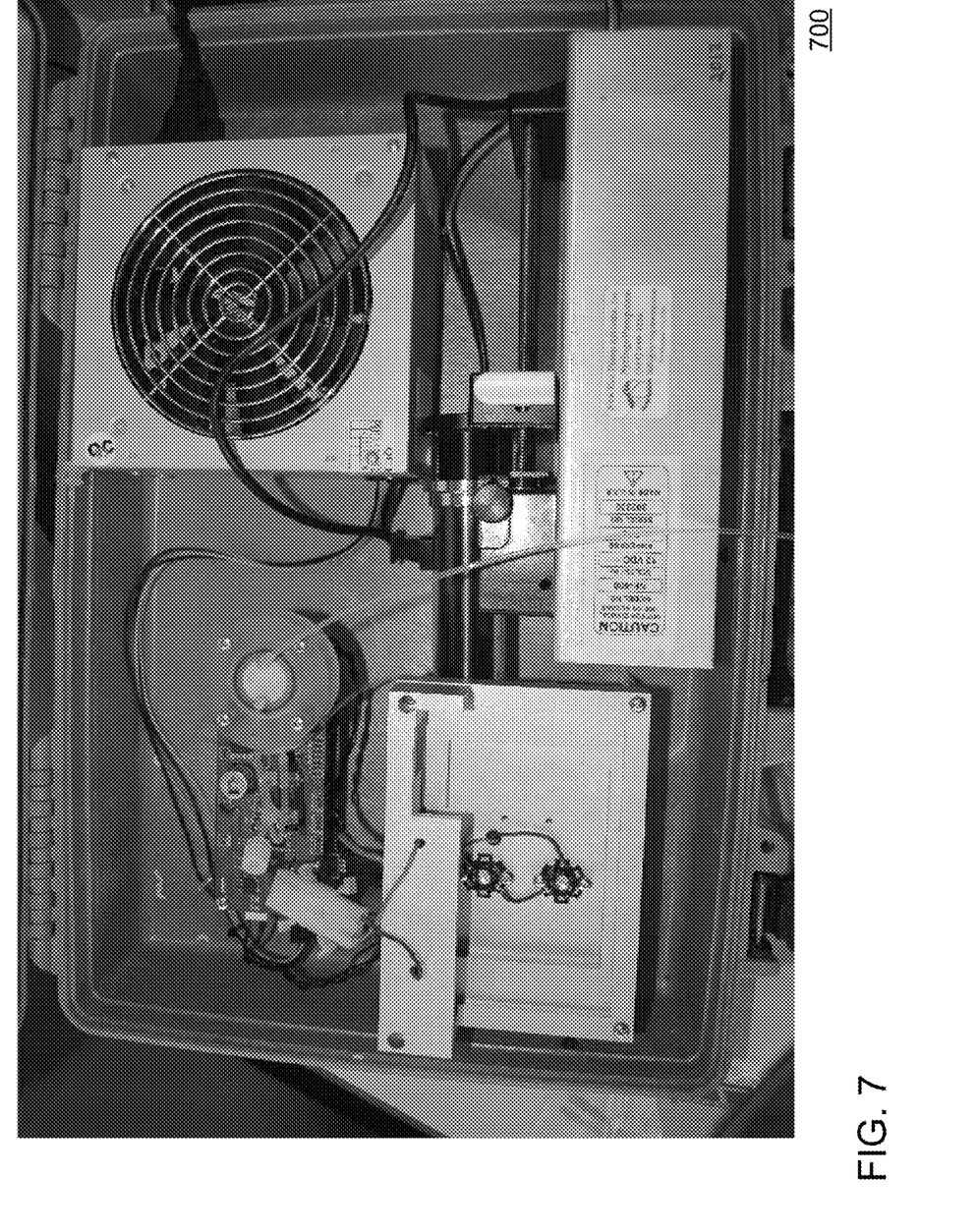
FIG. 7 illustrates a prototype apparatus for measuring nitric oxide in a fluid that incorporates one or more aspects and features of the invention.

A photograph of a prototype apparatus 700 of the invention, including one or more aspects and features described herein, is shown in FIG. 7. As seen, the components are contained within a case that is of relatively small size and is portable by hand.

In view of the foregoing, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. §112, ¶6 under U.S. patent law, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

What is claimed is:

1. A method for measuring a dissolved gas in a fluid comprising:
   adding the fluid into a sample chamber of a disposable cartridge configured to be coupled to a reusable instrument component having an electrochemical sensor;
   transferring the fluid from the sample chamber to a sample degassing chamber;
   liberating the dissolved gas from the fluid within the sample degassing chamber, wherein liquid and solid residue is retained within the sample degassing chamber following liberating of the dissolved gas;
   capturing the liberated gas in a carrier gas contained within the sample degassing chamber;
   providing the liberated gas in the carrier gas to the reusable instrument component; and
   measuring the dissolved gas concentration using the electrochemical sensor.

2. The method of claim 1, wherein the dissolved gas is nitric oxide.

3. The method of claim 1, wherein liberating the dissolved gas from the fluid includes:
   freeing the gas from its molecular bonds using electromagnetic radiation; and
   outgassing the dissolved gas from the fluid.

4. The method of claim 3, wherein using electromagnetic radiation includes using a light emitting diode.

5. The method of claim 3, wherein the outgassing includes heat vaporization.

6. The method of claim 1, wherein capturing the liberated gas includes capturing in an environment closed from ambient atmosphere.

7. An apparatus for measuring nitric oxide in a fluid, sample comprising:
   a disposable component for receiving the fluid sample, liberating dissolved gas in a fluid sample, and containing liquid or solid residue following liberation of dissolved gas for disposal with the disposable component; and
   a reusable instrument component comprising a pump, one or more valves, a nitric oxide sensor, one or more controls and one or more user interfaces;
   wherein the disposable component is insertable into the reusable instrument component to receive the liberated dissolved gas from the disposable component for evaluating the liberated dissolved gas with the nitric oxide sensor.

8. The apparatus of claim 7, wherein the disposable component is configured for a single use.

9. The apparatus of claim 7, wherein the disposable component includes means for liberating nitric oxide gas from the fluid.

10. The apparatus of claim 9, wherein the means for liberating nitric oxide gas from the fluid sample includes an electromagnetic radiation source.

11. The apparatus of claim 9, wherein the means for liberating nitric oxide gas from the fluid sample comprises a means for outgassing the nitric oxide gas from the fluid.

12. The apparatus of claim 7, wherein the one or more controls and a user interface comprising a microprocessor.

13. The apparatus of claim 7, wherein the nitric oxide sensor is an electrochemical sensor.

14. The apparatus of claim 7, wherein the apparatus includes a means for capturing the liberated dissolved gas.

15. The apparatus of claim 14, wherein the means for capturing the nitric oxide containing gas is closed to ambient atmosphere.

16. The apparatus of claim 7 wherein the reusable instrument component includes an electromagnetic radiation source.

17. The apparatus of claim 16 wherein the electromagnetic radiation source comprises a light emitting diode.

18. The apparatus of claim 7, wherein the disposable component includes a means for containing the liquid and solid components of the fluid sample.

19. The apparatus of claim 18, wherein the means for containing the liquid and solid components of the fluid sample is a gas permeable membrane.

* * * * *